(12) United States Patent
Wang

(10) Patent No.: US 8,921,346 B2
(45) Date of Patent: Dec. 30, 2014

(54) PREPARATION METHOD OF DROSPIRENONE

(75) Inventor: Jiazhen Wang, Taizhou (CN)

(73) Assignee: Taizhou Taifa Pharmaceuticals Co., Ltd., Zhejiang Provinve (CN)

( * ) Notice: Subject to any disclaimer, the term of this patent is extended or adjusted under 35 U.S.C. 154(b) by 203 days.

(21) Appl. No.: 13/579,229

(22) PCT Filed: Mar. 16, 2010

(86) PCT No.: PCT/CN2010/071074
§ 371 (c)(1),
(2), (4) Date: Aug. 15, 2012

(87) PCT Pub. No.: WO2011/113196
PCT Pub. Date: Sep. 22, 2011

(65) Prior Publication Data
US 2012/0316333 A1 Dec. 13, 2012

(51) Int. Cl.
*A61K 31/34* (2006.01)
*C07D 307/94* (2006.01)
*C07J 53/00* (2006.01)

(52) U.S. Cl.
CPC .................................. *C07J 53/008* (2013.01)
USPC ........................................... 514/173; 540/15

(58) Field of Classification Search
CPC .............................. A61K 31/34; C07D 307/94
USPC ............................................. 514/173; 540/15
See application file for complete search history.

(56) References Cited

FOREIGN PATENT DOCUMENTS

| CN | 1223662 A | 7/1999 |
|---|---|---|
| CN | 101092443 A | 12/2007 |
| CN | 101503455 A | 8/2009 |
| EP | 0075189 | 3/1983 |

*Primary Examiner* — Brenda Coleman
(74) *Attorney, Agent, or Firm* — Jacobson Holman PLLC; Jiwen Chen

(57) ABSTRACT

The present invention discloses the preparation method of drospirenone. 3β,5-dyhydroxy-6β,7β,15β, 16β-dimethylene- 5β-androstane-17,20-epoxy is taken as the raw material. It is subject to oxidization of the hydroxyl at the $3^{rd}$ position, ketalization of 3-ketone group, condensation reaction and deesterification to obtain carboxylic acid lactone, sulfonation of the hydroxyl at the $5^{th}$ position, and deketalization and desulphonation in the reaction system of glacial acetic acid and sodium acetate to produce the 3-keto-4-alkenyl compound, thus obtaining drospirenone. The preparation method of the invention has high intensification, reaction specificity, less by-products and high yield of products in each step, thus overcoming the disadvantages of low yield and unstable quality.

12 Claims, No Drawings

PREPARATION METHOD OF DROSPIRENONE

This is a U.S. national stage application of PCT Application No. PCT/CN2010/071074 under 35 U.S.C. 371, filed Mar. 16, 2010 in Chinese, which are hereby incorporated by reference.

FIELD OF THE INVENTION

The present invention relates to the field of chemical synthesis, especially the preparation method of drospirenone.

BACKGROUND OF THE INVENTION

Drospirenone has the chemical name of 6β,7β,15β,16β-dimethylene-3-oxo-17α-pregn-4-ene-21,17-carbolactone, CAs#:67392-87-4, molecular formula: $C_{24}H_{30}O_3$, molecular weight: 366.49, and its structural formula is as follows:

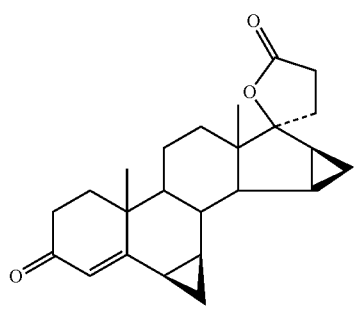

Drospirenone is the fourth-generation progestogen developed by German Schering, initially available in German in November, 2000 and now on the markets of United States of America and most European countries. This product has activities of both anti-mineralocorticoid and antiandrogen: the antiandrogen decreases the sebaceous gland activity and the adverse reaction; and the anti-mineralocorticoid lowers excretion of sodium and water, fluid retention and weight gain as well as symptoms associated with menstruation. Meanwhile, the drospirenone has little impact on blood pressure or blood lipid, and has the function of losing weight and maintaining health. Many women choose this product for better skin, hair, mood, and more stable weight. As it has these unique characteristics, now drospirenone has become the preferred contraceptive in foreign countries.

European patent EP0075189 discloses a synthetic method of drospirenone as follows:

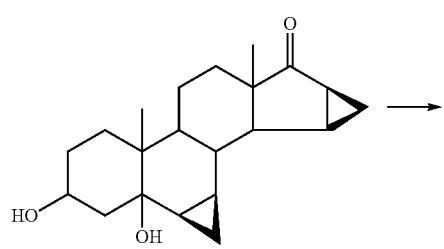

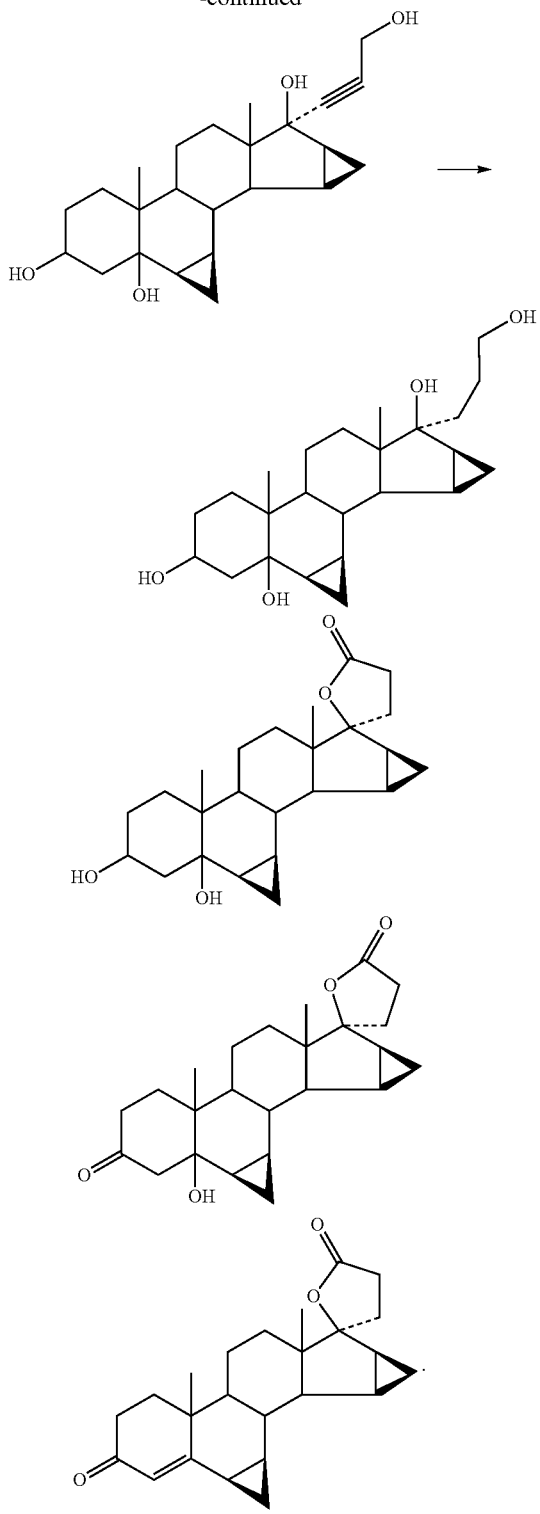

The synthetic method disclosed in the patent has potential safety risk as the explosive combustible catalyst and hydrogen are used. In addition, because the dehydration is conducted under the alkaline condition, this may cause the sipro ring to open and be re-arranged.

Chinese patent CN101092443 discloses a new synthetic method of drospirenone as follows:

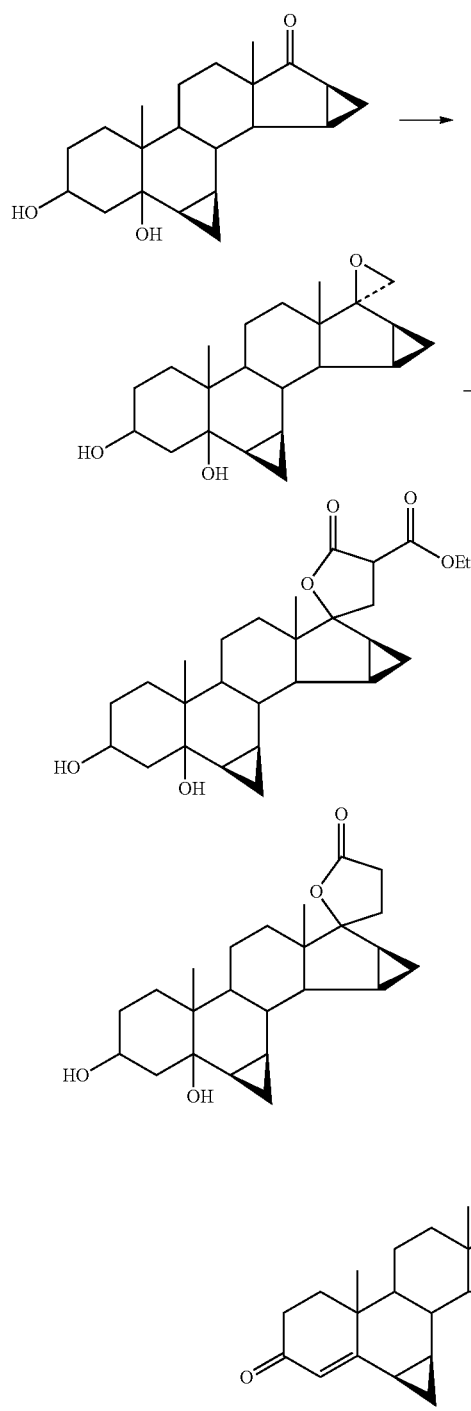

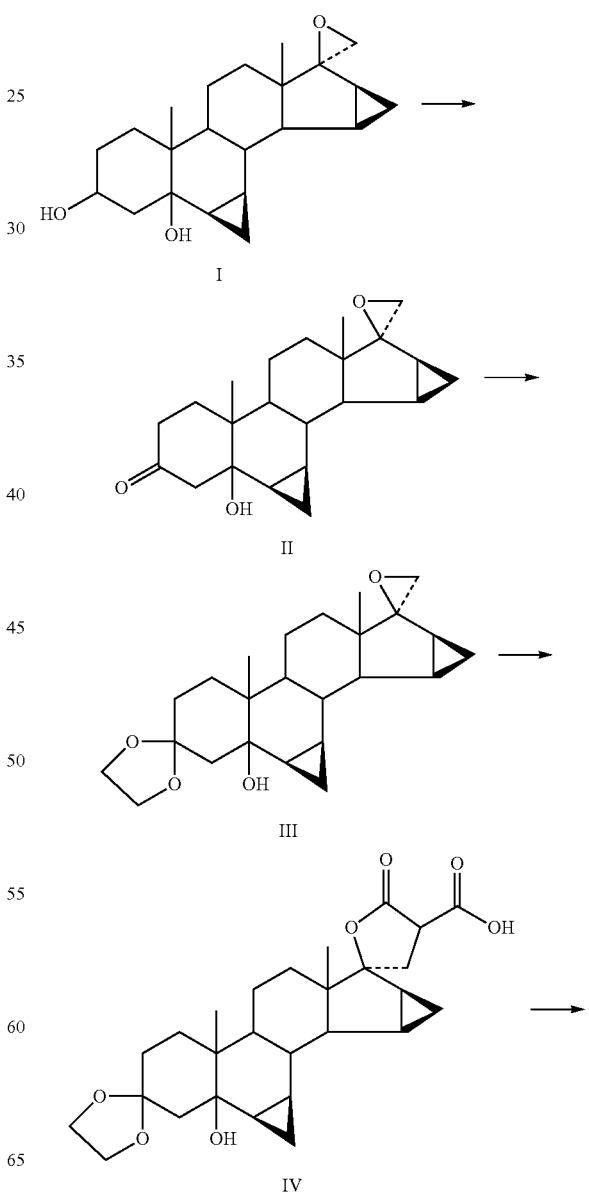

A preparation method of drospirenone comprising the following steps:

3β,5-dyhydroxy-6β,7β,15β,16β-dimethylene-5β-androstane-17,20-epoxy in Formula I is taken as the raw material (please refer to Chinese patent CN101092443 for the synthetic method of the raw material). The hydroxyl at the $3^{rd}$ position is oxidized to obtain the oxide in Formula II, and then the ketone group is protected by ketalization to obtain the ketal product in Formula III; the obtained ketal product is made into the compound in Formula IV after condensation reaction, and then the lactone compound in Formula V is obtained after deesterification; the hydroxyl at the $5^{th}$ position is subject to sulfonation and esterification to obtain the sulfonyl compound in the VI; and the deketalization and desulphonation are performed in the reaction system of glacial acetic acid and sodium acetate to produce the 3-keto-4-alkenyl compound, thus obtaining drospirenone in the formula VII.

In this method, the dehydration is also conducted under the alkaline, this may cause the sipro ring to open and be re-arranged. Moreover, the method is more complicated.

SUMMARY OF THE INVENTION

The present invention provides a preparation method of drospirenone which has a good reaction specificity to avoid the disadvantages of potential safety risk and easy re-arrangement of the existing methods.

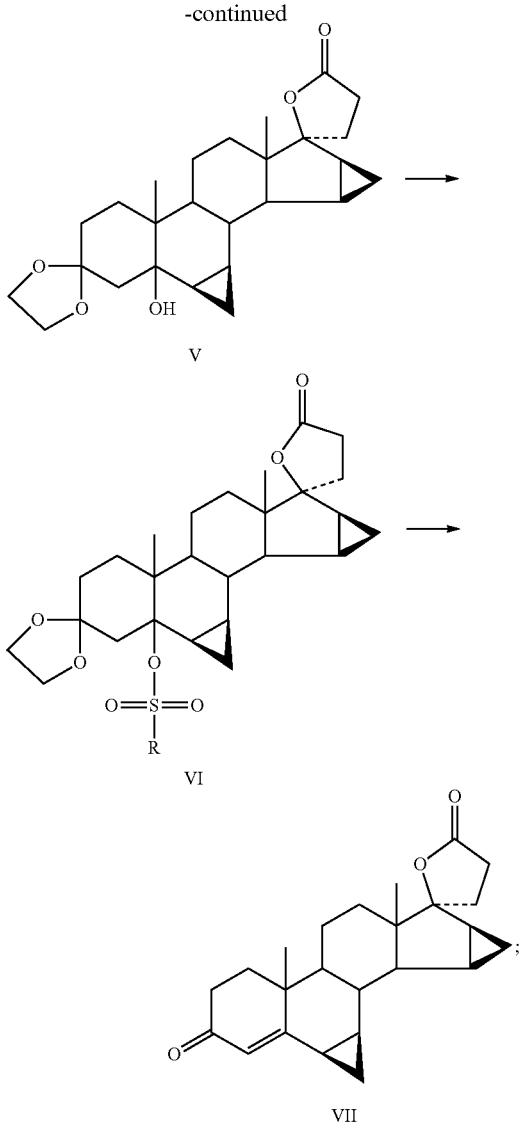

In Formula VI, R is $C_1$-$C_{10}$ alkyl, selected from one of phenyl, tolyl and methyl.

The preparation method of drospirenone comprises the following steps:

(1) 3β,5-dyhydroxy-6β,7β,15β,16β-dimethylene-5β-androstane-17,20-epoxy is taken as the raw material, and reacts with an oxidant in solvent at 0° C.-80° C. to obtain the oxide in Formula II;

(2) The oxide in Formula II, glycol and acid catalyst are mixed and subject to reflux reaction or the reaction with dehydrant at 0° C.-80° C. to obtain the ketal product in Formula III, so the product has better hydrophobicity and higher output;

(3) Alcoholic solution of dimethyl malonate is blended with miscible liquids of alcohol and sodium alcoholate at −10° C. to 30° C. (alcoholic solution of dimethyl malonate is preferably dripped into the mixture of alcohol and sodium alcoholate), and subject to heating and reflux reaction. The reactant is cooled down, put into the ketal product in Formula III, and subject to reaction at 0° C.-80° C. to produce the compound in Formula IV;

(4) The compound in Formula IV reacts with alkali metal salts halide in the presence of N,N-dimethylformamide and is subject to reflux reaction or reaction at 100° C.-180° C. to obtain the lactone compound in Formula V;

(5) The lactone compound in Formula V reacts with sulfonyl chloride compounds in the presence of pyridine at 0° C.-80° C. to obtain the sulfonyl compound in the VI;

(6) The sulfonyl compound in Formula VI is subject to reflux reaction in the reaction system of glacial acetic acid and sodium acetate to produce the drospirenone in Formula VII.

The process route can reduce the loss of products during water washing and prevent the adverse reaction, such as spiro ring and propyl ring damage during dehydration due to use of strong acid or alkali dehydration, by adopting sulfonylation-desulphonation method.

Preferably, the oxidant said in the step (1) is selected from one of sulfuric acid solution containing chromic anhydride, pyridine solution containing chromic anhydride, N-bromo-succinimide and so on.

The sulfuric acid solution containing chromic anhydride or pyridine solution containing chromic anhydride is prepared by mixing chromic anhydride and sulfuric acid or pyridine, and the oxidant solution of routine concentration in the field is applied to the preparation of the said solution.

The solvent is selected from one or more of acetone, pyridine, methanol, tert-butyl alcohol and so on.

The acid catalyst said in the step (2) is elected from one of p-toluenesulfonic acid, boron trifluoride-diethyl ether solution, sulfuric acid, sodium bisulfate and so on.

The dehydrant is triethyl orthoformate.

The weight ratio of oxide in Formula II to acid catalyst is 1:0.00005-0.1.

The weight ratio of oxide in Formula II to glycol is 1:2-10.

The reaction in step (2) can also be performed in organic solvents which can be some common solvents such as benzene, methylene chloride and so on.

The alcohol in step (3) is elected from one of methanol, ethanol and so on; and the sodium alcoholate is elected from one of sodium methoxide, sodium ethoxide and so on.

The alkali metal salts halide in step (4) is elected from one of lithium bromide, sodium chloride and so on.

The reaction system in step (4) can also be added with appropriate amount of water The sulfonyl chloride compound in step (5) is elected from one of benzene sulfonyl chloride, p-toluenesulfonyl chloride, methane sulfonyl chloride and so on.

The sodium acetate accounts for 9%-20% (mass percent) in the reaction system in step (6).

The reaction time is not strictly limited in the steps (1)-(6) of this invention. It can be considered as an end of the reaction when the reaction of one or a plurality of raw materials are completed by sampling at predetermined time with following up analysis through thin layer chromatography (TLC).

To ensure complete reaction, experiments show the reaction time in step (1) is often 1-3 hours;

The reaction time in step (2) is often 1-20 hours;

The reaction time after the ketal product in Formula III added in step (3) is often 3-25 hours;

The reaction time in step (4) is often 0.5-4 hours;

The reaction time in step (5) is often 0.5-3 hours;

The reaction time in step (6) is often 0.5-1 hours.

The amounts of raw materials in all steps are not strictly limited, generally in accordance with the stoichiometric ratio of reaction equation (i.e. mole ratio 1:1) or excess of partial raw materials.

The product in this invention has the following advantages:

The process route of the present invention has high intensification, reaction specificity, less by-products and high yield of products in each step, thus overcoming the disadvantages of low yield and unstable quality. Moreover, the production process is very safe and suitable for industrial production.

DESCRIPTION OF THE PREFERRED EMBODIMENT

The preparation method of the present invention is specifically described as follows, which does not limit the invention.

Embodiment 1

(1) 3β,5-dyhydroxy-6β,7β,15β,16β-dimethylene-5β-androstane-17,20-epoxy (compound in Formula I) of 5 g was dissolved in 50 ml pyridine, added into 50 ml pyridine solution containing 5 g chromic anhydride, evenly stirred, subject to reaction at 80° C. for 1 hour, placed overnight at room temperature, put into ice water, extracted and filtered to obtain 4.5 g oxide in Formula II.

(2) The oxide in Formula II of 4.5 g, dichloromethane of 50 ml, triethyl orthoformate of 5 ml were mixed with 10 ml glycol, added with 0.0025 g p-toluenesulfonic acid and stirred at room temperature for 3 hours to obtain 5 g ketal product in Formula III.

(3) The solution of 500 ml methanol and 20 g sodium methoxide is dripped with 70 ml methanol solution containing 60 ml dimethyl malonate at 0° C., subject to heating reflux reaction for 30 minutes, cooled down to room temperature, added with 20 g ketal product in Formula III (20 g ketal product in Formula III prepared by step (2)), stirred at room temperature for 3 hours, and then subject to heating and reflux reaction for 10 hours to obtain the compound in Formula IV.

(4) All of compound in Formula IV produced in last step was mixed with 120 ml DMF, 20 ml H$_2$O and 24 g lithium bromide, and subject to reflux reaction for 3.5 hours to obtain 22 g lactone compound in Formula V.

(5) The lactone compound in Formula V of 22 g was dissolved in 100 ml pyridine, added with 16 g benzene sulfonyl chloride, and subject to reaction at room temperature for 2 hours to obtain the sulfonyl compound in Formula VI.

(6) All of sulfonyl compound in the VI produced in the last step was mixed with 110 ml glacial acetic acid and 11 g sodium acetate, and subject to heating and reflux reaction for 30 minutes to obtain 18 g drospirenone in the Formula VII.

Embodiment 2

(1) 3β,5-dyhydroxy-6β,7β,15β,16β-dimethylene-5β-androstane-17,20-epoxy (compound in Formula I) of 5 g was dissolved in 150 ml acetone, added into the solution containing 5 g chromic anhydride, 15 ml water and 5 ml sulfuric acid, evenly stirred, and subject to reaction at 0° C. for 3 hours to obtain 4.7 g oxide in Formula II.

(2) The oxide in Formula II of 5 g (5 g oxide in Formula II prepared by step (1)), benzene of 150 ml, glycol of 10 ml were evenly mixed, added with 0.025 g p-toluenesulfonic acid and subject to reflux reaction for 20 hours to obtain 5.1 g ketal product in Formula III.

(3) The solution of 500 ml ethanol and 20 g sodium ethoxide was dripped with a 70 ml ethanol solution containing 60 ml dimethyl malonate at 0° C., subject to heating and reflux reaction for 20 minutes, cooled down to room temperature, added with 20 g ketal product in Formula III (20 g ketal product in Formula III prepared by step (2)), stirred at room temperature for 3 hours, and then subject to heating and reflux reaction for 20 hours to obtain the compound in Formula IV.

(4) All of compound in Formula IV produced in last step was mixed with 120 ml DMF, 20 ml H$_2$O and 24 g sodium chloride, and subject to reflux reaction for 3.5 hours to obtain 21.5 g lactone compound in Formula V.

(5) The lactone compound in Formula V of 20 g was dissolved in 100 ml pyridine, added with 16 g p-toluene-sulfonic acid chloride, and subjection to reaction at room temperature for 2 hours to obtain the sulfonyl compound in Formula VI.

(6) All of sulfonyl compound in the VI produced in the last step was mixed with 150 ml glacial acetic acid and 15 g sodium acetate, and subject to heating and reflux reaction for 60 minutes to obtain 17.2 g drospirenone in the Formula VII.

Embodiment 3

(1) 3β,5-dyhydroxy-6β,7β,15β,16β-dimethylene-5β-androstane-7,20-epoxy (compound in Formula I) of 10 g was dissolved in 150 ml tertiary butanol and 150 ml methanol, added with 2 g N-bromsucciniamide and appropriate amount of water, evenly stirred, and subject to reaction at room temperature for 3 hours to obtain 8.5 g oxide in Formula II.

(2) The oxide in Formula II of 8.5 g, triethyl orthoformate of 5 ml, and glycol of 50 ml were evenly mixed, added with 0.0005 g boron trifluoride-ether, and stirred at room temperature for 3 hours to obtain 9.5 g ketal product in Formula III.

(3) The solution of 500 ml ethanol and 20 g sodium ethoxide was dripped with 70 ml ethanol solution containing 60 ml dimethyl malonate at 0° C., subject to heating and reflux reaction for 20 minutes, cooled down to room temperature, added with 8 g ketal product in Formula III, stirred at room temperature for 3 hours, and then subject to heating and reflux reaction for 20 hours to obtain the compound in Formula IV.

(4) All of compound in Formula IV produced in last step was mixed with 120 ml DMF, 20 ml H$_2$O and 24 g sodium chloride, and subject to reflux reaction for 3.5 hours to obtain 8.5 g lactone compound in Formula V.

(5) The lactone compound in Formula V of 20 g (20 g lactone compound in Formula V prepared by step (4)) was dissolved in 100 ml pyridine, added with 10 g methane sulfonyl chloride, and subject to reaction at 0° C. for 2 hours to obtain the sulfonyl compound in Formula VI.

(6) All of sulfonyl compound in the VI produced in the last step was mixed with 150 ml glacial acetic acid and 30 g sodium acetate, and subject to heating and reflux reaction for 45 minutes to obtain 16 g drospirenone in the Formula VII.

Embodiment 4

(1) 3β,5-dyhydroxy-6β,7β,15β,16β-dimethylene-5β-androstane-17,20-epoxy (compound in Formula I) of 5 g was dissolved in 50 ml pyridine, added into 50 ml pyridine solution containing 5 g chromic anhydride, evenly stirred, subject to reaction at 80° C. for 1 hour, placed overnight at room temperature, put into ice water, extracted and filtered to obtain 4.4 g oxide in Formula II.

(2) The oxide in Formula II of 5 g (5 g oxide in Formula II prepared by step (1)), dichloromethane of 50 ml, triethyl orthoformate of 5 ml were evenly mixed with 10 ml glycol, added with 0.025 g sulfuric acid and stirred at room temperature for 3 hours to obtain 4.4 g ketal product in Formula III.

(3) The solution of 500 ml ethanol and 20 g sodium ethoxide was dripped with 70 ml methanol solution containing 60 ml dimethyl malonate at 0° C., subject to heating and reflux reaction for 30 minutes, cooled down to room temperature, added with 4 g ketal product in Formula III, stirred at room temperature for 3 hours, and then subject to heating and reflux reaction for 20 hours to obtain the compound in Formula IV.

(4) All of compound in Formula IV produced in last step was mixed with 30 ml DMF, 30 ml H$_2$O and 6 g lithium bromide, and subject to reflux reaction for 3.5 hours to obtain 4.2 g lactone compound in Formula V.

(5) The lactone compound in Formula V of 10 g (10 g lactone compound in Formula V prepared by step (4)) was dissolved in 50 ml pyridine, added with 6 g methane sulfonyl chloride, and subject to reaction at 5° C.-10° C. for 0.5 h to obtain the sulfonyl compound in Formula VI.

(6) All of sulfonyl compound in the VI produced in the last step was mixed with 150 ml glacial acetic acid and 20 g sodium acetate, and subject to heating and reflux reaction for 45 minutes to obtain 7.5 g drospirenone in the Formula VII.

Embodiment 5

(1) 3β,5-dyhydroxy-6β,7β,15β,16β-dimethylene-5β-androstane-17,20-epoxy (compound in Formula I) of 5 g was dissolved in 50 ml pyridine, added into 50 ml pyridine solution containing 5 g chromic anhydride, evenly stirred, subject to reaction at 80° C. for 1 hour, placed overnight at room temperature, put into ice water, extracted and filtered to obtain 4.6 g oxide in Formula II.

(2) The oxide in Formula II of 5 g (5 g oxide in Formula II prepared by step (1)), dichloromethane of 50 ml, triethyl orthoformate of 5 ml were evenly mixed with 10 ml glycol, added with 0.5 g sodium bisulfate, and stirred at room temperature for 3 hours to obtain 5.5 g ketal product in Formula III.

(3) The solution of 500 ml methanol and 20 g sodium methoxide was dripped with 70 ml methanol solution containing 60 ml dimethyl malonate at 0° C., subject to heating and reflux reaction for 30 minutes, cooled down to room temperature, added with 20 g ketal product in Formula III (20 g ketal product in Formula III prepared by step (2)), stirred at room temperature for 3 hours, and then subject to heating and reflux reaction for 20 hours to obtain the compound in Formula IV.

(4) All of compound in Formula IV produced in last step was mixed with 120 ml DMF, 20 ml $H_2O$ and 24 g lithium bromide, and subject to reflux reaction for 3.5 hours to obtain 20.5 g lactone compound in Formula V.

(5) The lactone compound in Formula V of 20 g was dissolved in 100 ml pyridine, added with 10 g methane sulfonyl chloride, and subject to reaction at 0° C.-5° C. for 1 hour to obtain the sulfonyl compound in Formula VI.

(6) All of sulfonyl compound in the VI produced in the last step was mixed with 150 ml glacial acetic acid and 25 g sodium acetate, and subject to heating and reflux reaction for 30 minutes to obtain 17 g drospirenone in the Formula VII.

Embodiment 6

(1) 3β,5-dyhydroxy-6β,7β,15β,16β-dimethylene-5β-androstane-17,20-epoxy (compound in Formula I) of 5 g was dissolved in 50 ml pyridine, added into 50 ml pyridine solution containing 5 g chromic anhydride, evenly stirred, subject to reaction at 10° C. for 2.5 hours, placed overnight at room temperature, put into ice water, extracted and filtered to obtain 4.5 g oxide in Formula II.

(2) The oxide in Formula II of 5 g (5 g oxide in Formula II prepared by step (1)), dichloromethane of 50 ml, triethyl orthoformate of 5 ml are evenly mixed with 10 ml glycol, added with 0.5 g sodium bisulfate and stirred at 0° C. for 15 hours to obtain 5.4 g ketal product in Formula III.

(3) The solution of 500 ml methanol and 20 g sodium methoxide was dripped with 70 ml methanol solution containing 60 ml dimethyl malonate at −10° C., subject to heating and reflux reaction for 30 minutes, cooled down to room temperature, added with 20 g ketal product in Formula III (20 g ketal product in Formula III prepared by step (2)), stirred at 0° C. for 3 hours, and then subject to heating and reflux reaction for 15 hours to obtain the compound in Formula IV.

(4) All of compound in Formula IV produced in last step was mixed with 120 ml DMF, 20 ml $H_2O$ and 24 g lithium bromide, and subject to reaction at 100° C. for 4 hours to obtain 20.2 g lactone compound in Formula V.

(5) The lactone compound in Formula V of 20 g was dissolved in 100 ml pyridine, added with 10 g methane sulfonyl chloride, and subject to reaction at 50° C. for 3 hours to obtain the sulfonyl compound in Formula VI.

(6) All of sulfonyl compound in the VI produced in the last step is mixed with 150 ml glacial acetic acid and 25 g sodium acetate, and subject to heating and reflux reaction for 30 minutes to obtain 16.5 g drospirenone in the Formula VII. psl Embodiment 7

(1) 3β,5-dyhydroxy-6β,7β,15β,16β-dimethylene-5β-androstane-17,20-epoxy (compound in Formula I) of 5 g was dissolved in 50 ml pyridine, added into 50 ml pyridine solution containing 5 g chromic anhydride, evenly stirred, subject to reaction at 65° C. for 1.5 hours, placed overnight at room temperature, put into ice water, extracted and filtered to obtain 4.4 g oxide in Formula II.

(2) The oxide in Formula II of 5 g (5 g oxide in Formula II prepared by step (1)), dichloromethane of 50 ml, triethyl orthoformate of 5 ml were evenly mixed with 10 ml glycol, added with 0.5 g sodium bisulfate and stirred at 55° C. for 10 hours to obtain 5.45 g ketal product in Formula III.

(3) The solution of 500 ml methanol and 20 g sodium methoxide was dripped with 70 ml methanol solution containing 60 ml dimethyl malonate at 15° C., subject to heating and reflux reaction for 30 min, cooled down to room temperature, added with 20 g ketal product in Formula III (20 g ketal product in Formula III prepared by step (2)), stirred at 55° C. for 3 hours, and then subject to heating and reflux reaction for 10 h to obtain the compound in Formula IV.

(4) All of compound in Formula IV produced in last step was mixed with 120 ml DMF, 20 ml $H_2O$ and 24 g lithium bromide, and subject to reaction at 140° C. for 2 hours to obtain 20.3 g lactone compound in Formula V.

(5) The lactone compound in Formula V of 20 g was dissolved in 100 ml pyridine, added with 10 g methane sulfonyl chloride, and subject to reaction at 65° C. for 2.5 hours to obtain the sulfonyl compound in Formula VI.

(6) All of sulfonyl compound in the VI produced in the last step was mixed with 150 ml glacial acetic acid and 25 g sodium acetate, and subject to heating and reflux reaction for 50 min to obtain 16.6 g drospirenone in the Formula VII.

Embodiment 8

(1) 3β,5-dyhydroxy-6β,7β,15β,16β-dimethylene-5β-androstane-17,20-epoxy (compound in Formula I) of 5 g was dissolved in 50 ml pyridine, added into 50 ml pyridine solution containing 5 g chromic anhydride, evenly stirred, subject to reaction at 35° C. for 2 hours, placed overnight at room temperature, put into ice water, extracted and filtered to obtain 4.35 g oxide in Formula II.

(2) The oxide in Formula II of 5 g (5 g oxide in Formula II prepared by step (1)), dichloromethane of 50 ml, triethyl orthoformate of 5 ml were mixed with 48 ml glycol, added with 0.5 g sodium bisulfate and stirred at 80° C. for 1 hour to obtain 5.5 g ketal product in Formula III.

(3) The solution of 500 ml methanol and 20 g sodium methoxide was dripped with 70 ml methanol solution containing 60 ml dimethyl malonate at 30° C., subject to heating and reflux reaction for 30 minutes, cooled down to room temperature, added with 20 g ketal product in Formula III (20 g ketal product in Formula III prepared by step (2)), stirred at 80° C. for 3 hours, and then subject to heating and reflux reaction for 8 hours to obtain the compound in Formula IV.

(4) All of compound in Formula IV produced in last step was mixed with 120 ml DMF, 20 ml $H_2O$ and 24 g lithium bromide, and subject to reaction at 180° C. for 0.5 hour to obtain 20.1 g lactone compound in Formula V.

(5) The lactone compound in Formula V of 20 g was dissolved in 100 ml pyridine, added with 10 g methane sulfonyl chloride, and subject to reaction at 80° C. for 1.5 hour to obtain the sulfonyl compound in Formula VI.

(6) All of sulfonyl compound in the VI produced in the last step was mixed with 150 ml glacial acetic acid and 25 g sodium acetate, and subject to heating and reflux reaction for 60 minutes to obtain 16.8 g drospirenone in the Formula VII.

The invention claimed is:

1. A preparation method of drospirenone, comprising the following steps:
providing 3β,5-dyhydroxy-6β,7β,15β,16β-dimethylene-5β-androstane-17,20-epoxy of Formula I as raw material; oxidizing a hydroxyl at the $3^{rd}$ position to obtain an oxide of Formula II, and then protecting the 3-ketone group by ketalization to obtain the ketal product of Formula III; the obtained ketal product being made into the compound of Formula, IV after condensation reaction, and then obtaining the lactone compound of Formula V after deesterification; the hydroxyl at the $5^{th}$ position being subject to sulfonation and esterification to obtain the sulfonyl compound of Formula VI; and the deketalization and desulphonation being performed in the reaction system of the glacial acetic acid and sodium acetate to produce a 3-keto-4-alkenyl compound, thus obtaining drospirenone of Formula VII I
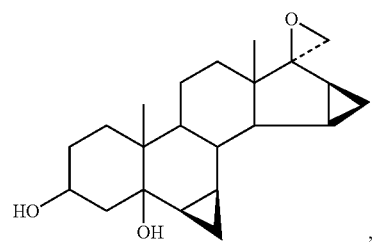

II
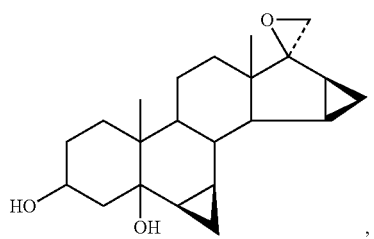

III
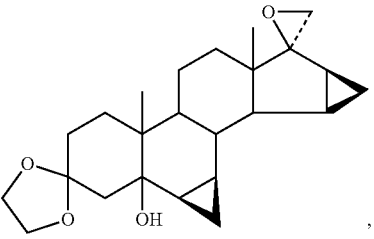

IV
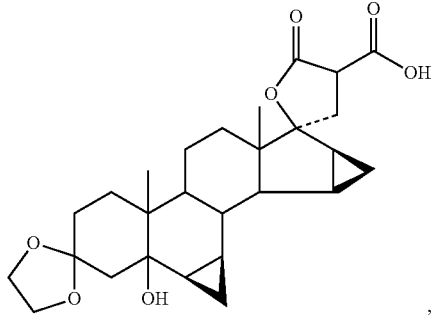

V
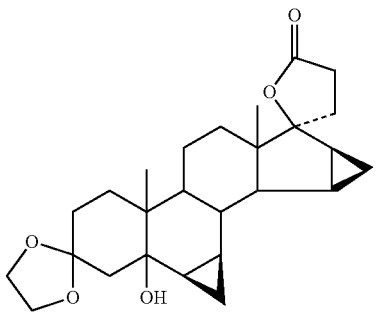

VI
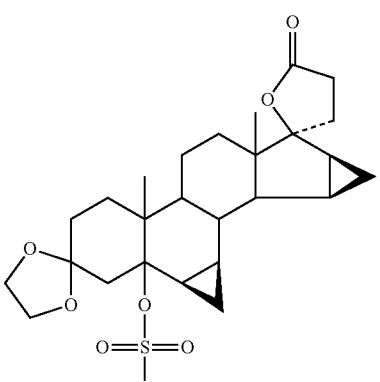

VII
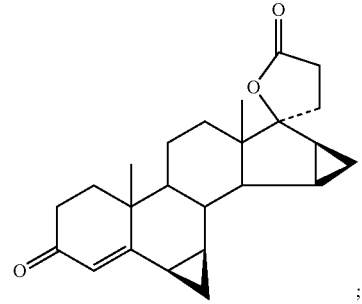

in formula VI, R being $C_1$-$C_{10}$ alkyl, phenyl, or tolyl.

2. The preparation method according to claim 1, wherein it comprises the following steps:
(1) 3β,5-dyhydroxy-6β,7β,15β,16β-dimethylene-5β-androstane-17,20 -epoxy is taken as the raw material, and reacts with an oxidant in solvent at 0° C. -80° C. to obtain the oxide of Formula II;
(2) the oxide in Formula II, glycol and acid catalyst are mixed and subject to reflux reaction or the reaction with dehydrant at 0° C.-80° C. to obtain the ketal product of Formula III;
(3) an alcoholic solution of dimethyl malonate is blended with miscible liquids of alcohol and sodium alcoholate at −10° C. to 30° C., and then subject to heating and reflux reaction, the reactant being cooled down, put into the ketal product in Formula III, and subject to reaction at 0° C.-80° C. to produce the compound of Formula IV;
(4) the compound in Formula IV reacts with alkali metal salts halide in the presence of N,N -dimethylformamide and is subject to reflux reaction or reaction at 100° C.-180° C. to obtain the lactone compound of Formula V;

(5) the lactone compound of Formula V reacts with sulfonyl chloride compounds in the presence of pyridine at 0° C.-80° C. to obtain the sulfonyl compound of the Formula VI;

(6) the sulfonyl compound of Formula VI is subject to reflux reaction in the reaction system of glacial acetic acid and sodium acetate to produce the drospirenone of Formula VII.

3. The preparation method according to claim 2, wherein the oxidant said in the step (1) is selected from one of sulfuric acid solution containing chromic anhydride, pyridine solution containing chromic anhydride, or N-bromosuccinimide.

4. The preparation method according to claim 2, wherein the solvent in the step (1) is selected from one or more of acetone, pyridine, methanol and tert-butyl alcohol.

5. The preparation method according to claim 2, wherein the acid catalyst in the step (2) is selected from one of p-toluenesulfonic acid, boron trifluoride-diethyl ether solution, sulfuric acid, sodium bisulfate; or the said dehydrant is triethyl orthoformate.

6. The preparation method according to claim 2, wherein the weight ratio of oxide of Formula II to acid catalyst said in the step (2) is 1:0.00005-0.1; and the weight ratio of oxide of Formula II to glycol is 1:2-10.

7. The preparation method according to claim 2, wherein the alcohol in step (3) is methanol or ethanol; and the sodium alcoholate is sodium methoxide or sodium ethoxide.

8. The preparation method according to claim 2, wherein the alkali metal salts halide in step (4) is selected from lithium bromide or sodium chloride.

9. The preparation method according to claim 2, wherein the sulfonyl chloride compounds in step (5) is selected from one of benzene sulfonyl chloride, p-toluenesulfonyl chloride and methanesulfonyl chloride; and R in Formula VI is selected from one of phenyl, tolyl and methyl.

10. The preparation method according to claim 1, wherein the sodium acetate accounts for 9%-20% (mass percent) in the reaction system in step (6).

11. The preparation method according to claim 5, wherein the weight ratio of oxide of Formula II to acid catalyst said in the step (2) is 1:0.00005-0.1; and the weight ratio of oxide of Formula II to glycol is 1:2-10.

12. The preparation method according to claim 2, wherein the sodium acetate accounts for 9%-20% (mass percent) in the reaction system in step (6).

* * * * *